United States Patent [19]

Meyer

[11] 4,307,056
[45] Dec. 22, 1981

[54] METHOD FOR MAKING ARTIFICIAL LIMB SOCKETS

[76] Inventor: Theodore C. Meyer, 16237 Lasher, Detroit, Mich. 48219

[21] Appl. No.: 157,327

[22] Filed: Jun. 9, 1980

[51] Int. Cl.³ ............................................. B29C 1/02
[52] U.S. Cl. ................................... 264/222; 3/17 R; 264/DIG. 30
[58] Field of Search ...................... 264/222, DIG. 30; 3/17 R, 18, 19

[56] References Cited

U.S. PATENT DOCUMENTS

| | | |
|---|---|---|
| 1,693,091 | 11/1928 | Loth . |
| 1,907,511 | 5/1933 | Davies . |
| 2,202,598 | 5/1940 | Peterson . |
| 3,909,855 | 10/1975 | Barredo ................................ 3/16 |

*Primary Examiner*—James B. Lowe

*Attorney, Agent, or Firm*—Basile, Weintraub & Hanlon

[57] ABSTRACT

A method and device for making artificial limb sockets is disclosed. To form the socket, the patient's below the knee stump is covered with a pair of stockinettes and a balloon is invaginated thereover to form a smooth surface for producing a mold of the stump. A plaster mold is formed over the stump and removed before the plaster has totally hardened. A device comprising a caliper for measuring the dimension across the patient's adductor tubercle is applied to the mold before removal from the stump. After removal from the patient's stump the adductor tubercle dimension is reestablished using the caliper before the plaster hardens. The mold is employed to form a casting of the patient's stump and the accurate reproduction of the adductor tubercle dimension allows the formation of a satisfactory supracondylar suspension.

2 Claims, 8 Drawing Figures

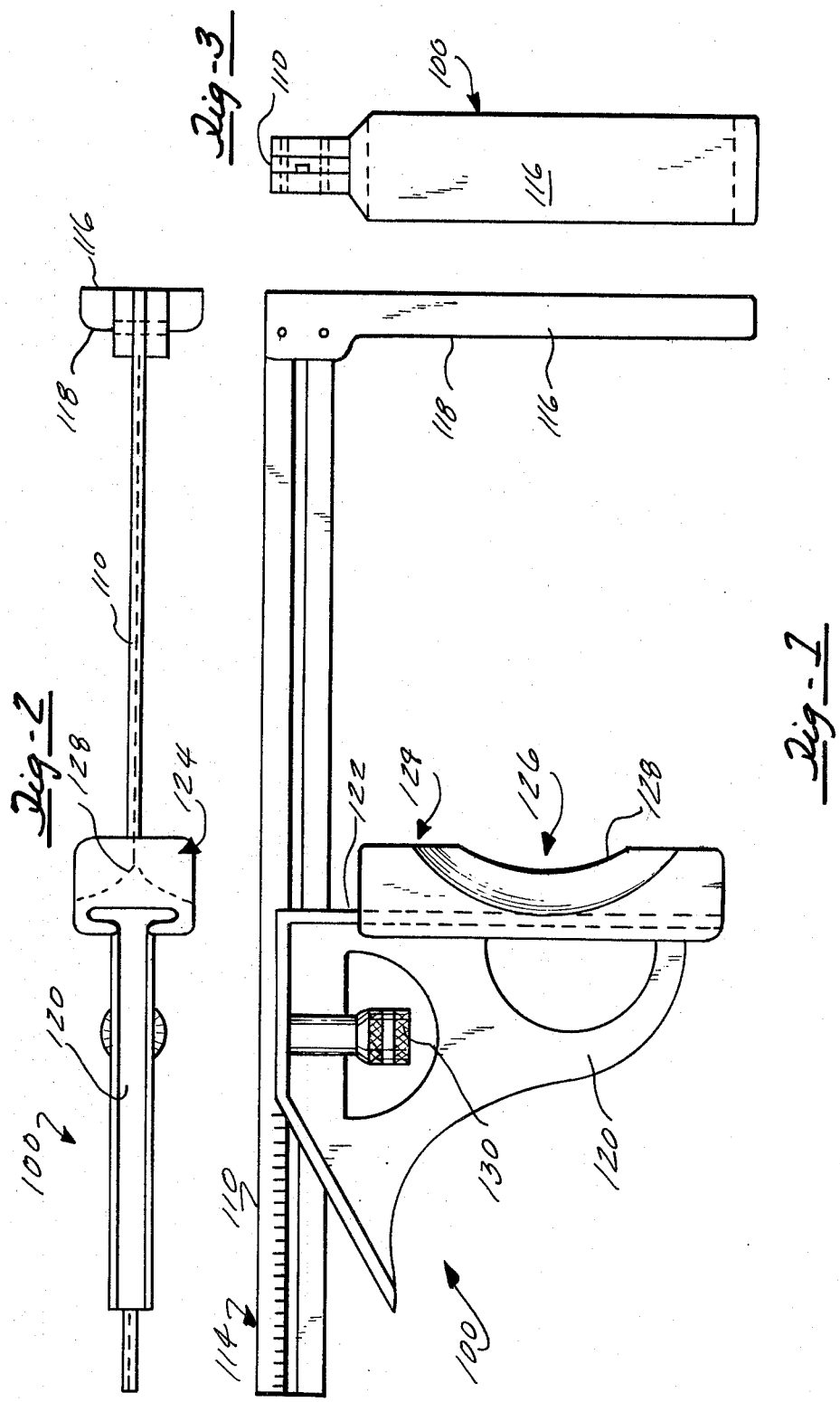

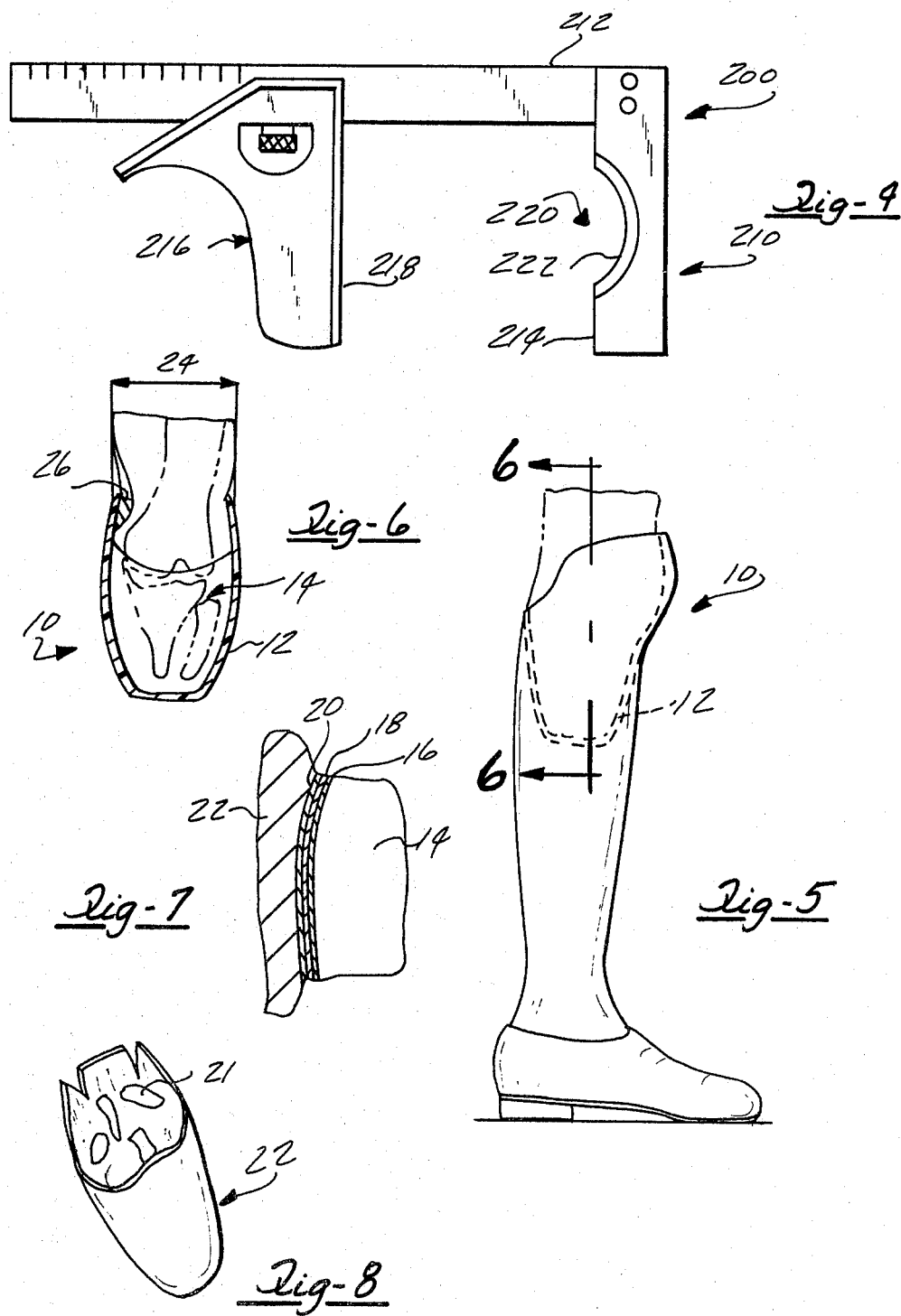

METHOD FOR MAKING ARTIFICIAL LIMB SOCKETS

BACKGROUND OF THE INVENTION

I. Field of the Invention

The present invention generally relates to the field of below the knee prosthetics and, in particular, the present invention is concerned with a method and device for making artificial limb sockets for below the knee amputations.

II. Description of the Prior Art

Sockets for artificial limbs in the prior art have been made from leather, wood, plastic wood, plastic and combinations of these materials. Examples of artificial limb sockets of this type are disclosed in U.S. Pat. Nos: 1,861,311, 2,202,598, 2,253,040, 2,402,327, 2,669,728, 1,693,091, and 1,153,532. U.S. Pat. No. 1,907,511 discloses a socket for an artificial limb made from nitro cellulose material. U.S. Pat. No. 3,909,855 discloses a below the knee prosthesis wherein the prosthesis is held to the leg by a loop passing over the knee of the patient. In general, artificial limb sockets in the prior art have been formed by first making a plaster mold of the patient's stump and then casting a replica of the patient's stump utilizing the mold. Boney prominences are identified and built up on the casting and a socket of leather or other suitable material is formed over the built up casting.

SUMMARY OF THE INVENTION

The present invention, which will be described in greater detail hereinafter, comprises a method and device for making artificial limb sockets for below the knee amputations. The socket of the present invention utilizes a supracondylar suspension wherein the prosthesis is secured to the stump of the patient utilizing a wedge at the adductor tubercle. To form a satisfactory supracondylar suspension it is necessary that the casting of the patient's stump accurately reproduce the adductor tubercle dimension. The present invention teaches the use of a caliper to measure the dimension across the adductor tubercle of a mold formed over the patient's stump. The mold is removed from the stump before hardening and the process of removing the mold enlarges the adductor tubercle dimension as the mold is pulled over the patient's knee. Once the mold has been removed from the stump the caliper is employed to restore the adductor tubercle dimension to that measured before removal from the stump, and an accurate mold of the patient's stump is thereby attained.

It is therefore a primary object of the present invention to provide a new and improved socket for below the knee prosthesis.

It is a further object of the present invention to provide such a socket for below the knee prosthesis that accurately duplicates the patient's adductor tubercle dimension.

It is yet another object of the present invention to provide such a socket for below the knee prosthesis that allows the use of a supracondylar suspension for the prosthesis.

Further objects, advantages, and applications of the present invention will become apparent to those skilled in the art of below the knee prosthesis when the accompanying description of one example of the best mode contemplated for practicing the invention is read in conjunction with the accompanying drawings.

BRIEF DESCRIPTION OF THE DRAWINGS

In the drawing like reference numbers refer to like parts throughout the several views, and wherein:

FIG. 1 illustrates a side view of the caliper of the present invention;

FIG. 2 illustrates a top view of the caliper of FIG. 1;

FIG. 3 illustrates an end view of the caliper of FIG. 1;

FIG. 4 illustrates an alternate embodiment of the caliper of the present invention;

FIG. 5 illustrates an artificial limb utilizing the prosthesis of the present invention;

FIG. 6 illustrates a cross sectional view taken along the lines 6—6 of FIG. 5;

FIG. 7 illustrates an enlarged, broken, cross sectional view through a mold formed over the stump of the patient; and FIG. 8 illustrates a perspective view of the mold of FIG. 7 after removal from the stump.

DESCRIPTION OF THE PREFERRED EMBODIMENT

The below the knee prosthesis that produces the most natural gait and the greatest degree of comfort for the patient utilizes a supracondylar suspension and a wedge at the adductor tubercle to attach the prosthesis to the stump of the patient in a secure manner. To utilize a supracondylar suspension it is necessary that the socket of the prosthesis accurately reproduce the patient's adductor tubercle dimension. The method and device of the present invention is utilized to accurately reproduce the patient's adductor tubercle dimension.

Referring now to the drawing, and in particular to FIGS. 5, 6, 7 and 8 there is illustrated at 10 the method for forming the socket 12 for a supracondylar suspension. The method for forming artificial limb sockets for below the knee amputation comprises the steps of:

covering a stump 14 (FIG. 7) with one or more stockinettes 16, 18;

inflating a balloon 20 having sufficient size to enclose the stump 14;

invaginating the balloon 20 over the stump 14 and stockinettes 16, 18 while inflated thereby inverting the balloon;

marking the boney prominences 21 of the stump on the balloon using a colored ink that will readily transfer to an abutting surface;

applying a bandage of cotton soaked in plaster of paris to the balloon to form a mold 22;

measuring the dimension 24 across the outside of the mold 22 at the adductor tubercle before the mold 22 hardens;

recording the adductor tubercle dimension 24;

cutting the mold 22 in one or more places behind the knee and removing the mold from the stump 14 before the mold 22 hardens;

reestablishing the adductor tubercle dimension 24 before the mold 22 hardens;

making a casting of the stump using the hardened mold;

adding material to the boney prominence areas 21 for comfort;

applying polyester over the stump casting to form a stump socket for an artificial limb;

in the preferred embodiment, to produce a supracondylar suspension, a wedge 26 of resilient material such as sponge rubber is heat formed to the stump casting on the medial side of the stump at the adductor tubercle prior to forming the stump socket. As shown in FIG. 6 of the drawing the wedge 26 secures the socket to the stump when it is in place, but allows easy removal of the socket 12 from the stump 14 once the wedge 26 has been removed.

As shown in FIGS. 1, 2, and 3 of the drawing, the adductor tubercle dimension 24 is measured and reestablished by a caliper 100. The caliper 100 comprises a linear scale 110 having measurement indicia 114 thereon. An upright end piece 116 is affixed to the end of the scale 110 and includes a transverse wall 118 perpendicular to the scale 110. A movable upright anvil 120 is disposed parallel to the end piece 116 and is slidably engageable with the scale and includes an opposed wall 122 parallel to the transverse wall 188. The movable anvil 120 is movable along the scale 110 toward and away from the transverse wall 118 to aid in measuring the adductor tubercle dimension.

The caliper 100 further includes, in a preferred embodiment, a transversely movable slide 24 slidingly engageable with the opposed wall 122. The slide 124 includes an arcuate recess 126 opposed to the transverse wall formed in the slide 124 by a narrow central wall 128. The slide 124 progressively increases in thickness from the narrow central wall 128 in a concave arcuate manner in a direction opposed to the transverse wall 118. In a preferred embodiment a locking screw 130 is provided to selectively lock the anvil 120 to the scale 110.

In an alternate embodiment illustrated in FIG. 4, a caliper 200 comprises a fixed upright member 210 fixedly attached to an end of a scale 212 including a fixed transverse wall 214 on a scale side perpendicular to the scale 212. An upright movable member 216 slidingly engages the scale 212 with the upright movable member including a movable transverse wall 218 parallel and opposed to the fixed transverse wall 214. The caliper 200 further includes a concave recess 220 formed in one of the transverse walls 214 or 218 with the recess 220 defined by a thin central wall 222 tapering with increasing thickness toward its associated member. While the concave recess 220 is illustrated in FIG. 4 as associated with the fixed upright member 210, it is obvious to the skilled artisan that the caliper will perform with equal efficiency with the recess 220 formed in either the fixed upright member 210 or the movable member 216.

It can thus be seen that the present invention has provided a new and improved method and device for making artificial limb sockets for below the knee amputations. The method and device of the present invention enables the formation of a mold of the stump of the patient that accurately reproduces the adductor tubercle dimension which allows the efficient formation of a supracondylar suspension.

It should be understood by those skilled in the art of below the knee prothesis that other forms of the Applicant's invention may be had, all coming within the spirit of the invention and the scope of the appended claims.

Having thus described my invention what I claim is:
1. A method for making artificial limb sockets for below the knee amputations comprising the steps of:
   covering a stump with one or more stockinettes;
   inflating a balloon having sufficient size to enclose the stump;
   invaginating the balloon over the stump and stockinettes by pushing the balloon over the stump while inflated thereby inverting said balloon;
   making boney prominences of the stump on the balloon using an indelible pencil that transfers to an abutting surface;
   applying a bandage of cotton soaked in plaster of paris to the balloon to form a mold;
   measuring the dimension across the outside of the mold at the adductor tubercle before the mold hardens;
   recording the adductor tubercle dimension;
   cutting the mold in one or more places behind the knee and removing the mold from the stump before the mold hardens;
   reestablishing the adductor tubercle dimension before the mold hardens;
   making a casting of the stump using the hardened mold;
   adding material to the boney prominence areas for comfort; and
   applying polyester over the stump casting to form a stump socket for an artificial limb.
2. The method as defined in claim 1 comprising an additional step of:
   heat forming a wedge of resilient material on the medial side of the stump casting at the adductor tubercle prior to forming the stump socket to provide a supracondylar suspension.

* * * * *